United States Patent
Amemiya

(10) Patent No.: US 6,669,634 B2
(45) Date of Patent: Dec. 30, 2003

(54) ULTRASONIC IMAGING APPARATUS

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 109 days.

(21) Appl. No.: 10/039,822

(22) Filed: Oct. 26, 2001

(65) Prior Publication Data

US 2002/0077548 A1 Jun. 20, 2002

(30) Foreign Application Priority Data

Dec. 18, 2000 (JP) ........................................ 2000-383674

(51) Int. Cl.7 ................................................. A61B 8/00
(52) U.S. Cl. ....................................... 600/437; 600/443
(58) Field of Search ................................ 606/159, 167; 128/916, 922; 600/463, 459, 447; 73/625, 226

(56) References Cited

U.S. PATENT DOCUMENTS

| | | | | | |
|---|---|---|---|---|---|
| 5,251,631 | A | * | 10/1993 | Tsuchiko et al. | 600/447 |
| 5,295,485 | A | * | 3/1994 | Shinomura et al. | 600/443 |
| 5,758,649 | A | * | 6/1998 | Iwashita et al. | 600/459 |
| 5,872,557 | A | * | 2/1999 | Wiemer et al. | 345/156 |
| 5,957,846 | A | * | 9/1999 | Chiang et al. | 600/447 |
| 6,159,150 | A | * | 12/2000 | Yale et al. | 600/437 |
| 6,251,073 | B1 | * | 6/2001 | Imran et al. | 600/443 |
| 6,440,072 | B1 | * | 8/2002 | Schuman et al. | 600/437 |

* cited by examiner

Primary Examiner—Francis J. Jaworski
(74) Attorney, Agent, or Firm—Moonray Kojima

(57) ABSTRACT

In order to provide an ultrasonic imaging apparatus that responds to the requirement for both portability and versatility, the ultrasonic imaging apparatus includes a portable imaging apparatus 100 comprising ultrasonic imaging means, and a support apparatus 500 which comprises supporting means for supporting extension of functions of the imaging apparatus, and which is electrically connected to and mechanically joined to the imaging apparatus so that it can be removably combined with the imaging apparatus.

12 Claims, 5 Drawing Sheets

ULTRASONIC IMAGING APPARATUS

BACKGROUND OF THE INVENTION

The present invention relates to an ultrasonic imaging apparatus, and particularly to an ultrasonic imaging apparatus consisting of two sections that can be separated and combined.

RELATED ART

In an ultrasonic imaging apparatus, the interior of an object being imaged is scanned by a pulsed ultrasonic beam and an echo is received, image data corresponding to the intensity of the echo is obtained, and a "B-mode" image is produced from the image data. This technique is sometimes referred to as B-mode imaging.

Moreover, a Doppler shift in the echo of the pulsed ultrasound is determined, and a color image representing the flow velocity distribution of blood flow etc., i.e., a "color Doppler" image, is produced based on the Doppler shift. Alternatively, a color image representing the power of the Doppler signal, i.e., a "power Doppler" image, is produced. This technique is sometimes referred to as pulsed Doppler imaging.

Furthermore, a Doppler shift in an echo of continuous wave (CW) ultrasound is determined, and is represented as a frequency spectrum image and as a Doppler sound. This technique is sometimes referred to as continuous wave Doppler imaging.

The image and sound obtained by such imaging are saved in a storage medium or a recording medium as imaging data, and read out as required and displayed on a display device for diagnosis. In an ultrasonic imaging apparatus having network accessing means, the imaging data may be saved on a server in a network for permitting other terminals connected to the network to use the imaging data.

Improvements in semiconductor IC integration and electronic part miniaturization have led to progressive reduction of the size and weight of ultrasonic imaging apparatuses. However, aside from those having simplified functions, general-purpose ultrasonic imaging apparatuses, which can perform all of the B-mode imaging, pulsed Doppler imaging and continuous wave Doppler imaging, can save imaging data, and enable network access, have not yet achieved sufficient size and weight reduction for portability.

SUMMARY OF THE INVENTION

It is therefore an object of the present invention to provide an ultrasonic imaging apparatus that responds to the requirement for both portability and versatility.

(1) In accordance with one aspect to solve the aforementioned problem, the present invention is an ultrasonic imaging apparatus comprising: a portable imaging apparatus comprising ultrasonic imaging means; and a support apparatus which comprises supporting means for supporting extension of functions of the imaging apparatus, and which is electrically connected to and mechanically joined to the imaging apparatus so that it can be removably combined with the imaging apparatus.

In the invention of this aspect, since a portable imaging apparatus comprising ultrasonic imaging means, and a support apparatus comprising supporting means for extending the functions of the imaging apparatus can be removably combined, the imaging apparatus can be removed from the support apparatus for carrying, and ultrasonic imaging can be performed at a site to which the imaging apparatus is carried. Moreover, when the imaging apparatus is used with the support apparatus combined, the functions of the imaging apparatus are extended by support from the support apparatus and the apparatus is imparted with versatility.

(2) In accordance with another aspect to solve the aforementioned problem, the present invention is the ultrasonic imaging apparatus as described regarding (1), wherein the imaging apparatus has a pair of surfaces that can be folded so that the surfaces face each other.

In the invention of this aspect, since the imaging apparatus has a pair of surfaces that can be folded so that the surfaces face each other, it can be folded for carrying.

(3) In accordance with still another aspect to solve the aforementioned problem, the present invention is the ultrasonic imaging apparatus as described regarding (2), wherein one surface of the pair of surfaces is provided with a display section and the other is provided with an operating section.

In the invention of this aspect, since one surface of the foldable pair of surfaces is provided with a display section and the other is provided with an operating section, the operating section can be manipulated while observing the display section with the pair of folded surfaces opened.

(4) In accordance with still another aspect to solve the aforementioned problem, the present invention is the ultrasonic imaging apparatus as described regarding any one of (1)–(3), wherein the support apparatus has a mounting portion for mounting the imaging apparatus.

In the invention of this aspect, since the support apparatus has a mounting portion for the imaging apparatus, the support apparatus and the imaging apparatus can be suitably combined.

(5) In accordance with still another aspect to solve the aforementioned problem, the present invention is the ultrasonic imaging apparatus as described regarding (4), wherein the mounting portion has a connecting portion for electrically connecting the imaging apparatus and the support apparatus.

In the invention of this aspect, since the mounting portion has a connecting portion for electrically connecting the imaging apparatus and the support apparatus, the mounting spontaneously forms electrical connection.

(6) In accordance with still another aspect to solve the aforementioned problem, the present invention is the ultrasonic imaging apparatus as described regarding (5), wherein the mounting portion has a joining portion for mechanically joining the imaging apparatus and the support apparatus.

In the invention of this aspect, since the mounting portion has a joining portion for mechanically joining the imaging apparatus and the support apparatus, the mounting spontaneously forms a mechanical joint.

(7) In accordance with still another aspect to solve the aforementioned problem, the present invention is the ultrasonic imaging apparatus as described regarding any one of (1)–(6), wherein the imaging apparatus and the support apparatus have individual CPU's operating under respective OS's that are different in kind from each other.

In the invention of this aspect, since the imaging apparatus and the support apparatus have individual CPU's operating under respective OS's that are different in kind from each other, the imaging apparatus and the support apparatus can be provided with respective CPU's and OS's that are suitable for their scales.

(8) In accordance with still another aspect to solve the aforementioned problem, the present invention is the ultrasonic imaging apparatus as described regarding (7), wherein the OS for the CPU in the imaging apparatus has a simpler configuration than the OS for the CPU in the support apparatus.

In the invention of this aspect, since an OS having a simpler configuration than the OS for the CPU in the support apparatus is employed as the OS for the CPU in the imaging apparatus, the imaging apparatus can be provided with a CPU and OS having a scale suitable for its portability.

(9) In accordance with still another aspect to solve the aforementioned problem, the present invention is the ultrasonic imaging apparatus as described regarding any one of (1)–(8), wherein the imaging apparatus is operated by power supplied from a direct current power supply.

In the invention of this aspect, since the imaging apparatus is operated by power supplied from a direct current power supply, a battery can be used for the power supply.

(10) In accordance with still another aspect to solve the aforementioned problem, the present invention is the ultrasonic imaging apparatus as described regarding (9), wherein the direct current power supply is a battery built in the imaging apparatus.

In the invention of this aspect, since the imaging apparatus is operated by power supplied from a built-in battery, the imaging apparatus can be used even at a site not equipped with a power supply.

(11) In accordance with still another aspect to solve the aforementioned problem, the present invention is the ultrasonic imaging apparatus as described regarding any one of (1)–(10), wherein the support apparatus is operated by power supplied from an alternating current power supply.

In the invention of this aspect, since the support apparatus is operated by power supplied from an alternating current power supply, a commercial alternating current power supply can be used.

(12) In accordance with still another aspect to solve the aforementioned problem, the present invention is the ultrasonic imaging apparatus as described regarding any one of (1)–(11), wherein the supporting means in the support apparatus comprises means for supplying power to the imaging apparatus.

In the invention of this aspect, since the support apparatus supplies power to the imaging apparatus, the imaging apparatus need not be independently supplied with power.

(13) In accordance with still another aspect to solve the aforementioned problem, the present invention is the ultrasonic imaging apparatus as described regarding any one of (1)–(12), wherein the supporting means in the support apparatus comprises means for supplying high voltage power to the imaging apparatus.

In the invention of this aspect, since the support apparatus supplies high voltage power to the imaging apparatus, the imaging apparatus need not have a high voltage generating section.

(14) In accordance with still another aspect to solve the aforementioned problem, the present invention is the ultrasonic imaging apparatus as described regarding any one of (1)–(13), wherein the supporting means in the support apparatus comprises means for supplying power to an external device.

In the invention of this aspect, since the support apparatus supplies power to an external device, the external device need not be independently supplied with power.

(15) In accordance with still another aspect to solve the aforementioned problem, the present invention is the ultrasonic imaging apparatus as described regarding any one of (12)–(14), wherein the means for supplying power comprises means for insulating a primary and a secondary of a power supply path.

In the invention of this aspect, since the primary and secondary of the power supply path from the support apparatus are insulated, electric leakage across different systems can be prevented.

(16) In accordance with still another aspect to solve the aforementioned problem, the present invention is the ultrasonic imaging apparatus as described regarding any one of (1)–(15), wherein the ultrasonic imaging means in the imaging apparatus and the supporting means in the support apparatus comprise means for performing data communication between the imaging apparatus and the support apparatus.

In the invention of this aspect, since data communication is performed between the imaging apparatus and the support apparatus, support of the imaging apparatus by the support apparatus can be suitably achieved.

(17) In accordance with still another aspect to solve the aforementioned problem, the present invention is the ultrasonic imaging apparatus as described regarding any one of (1)–(16), wherein the supporting means in the support apparatus comprises means for performing data communication with an external device.

In the invention of this aspect, since the support apparatus performs data communication with an external device, cooperation with the external device can be suitably achieved.

(18) In accordance with still another aspect to solve the aforementioned problem, the present invention is the ultrasonic imaging apparatus as described regarding (16) or (17), wherein the means for performing data communication comprises means for insulating a primary and a secondary of a data communication path.

In the invention of this aspect, since the primary and secondary of the data communication path from the support apparatus are insulated, electric leakage across different systems can be prevented.

(19) In accordance with still another aspect to solve the aforementioned problem, the present invention is the ultrasonic imaging apparatus as described regarding any one of (1)–(18), wherein the supporting means in the support apparatus comprises means for recording an image captured by the imaging apparatus.

In the invention of this aspect, since an image captured by the imaging apparatus is recorded by the support apparatus, the imaging apparatus need not record the image.

(20) In accordance with still another aspect to solve the aforementioned problem, the present invention is the ultrasonic imaging apparatus as described regarding any one of (1)–(19), wherein the supporting means in the support apparatus comprises means for managing an image captured by the imaging apparatus.

In the invention of this aspect, since an image captured by the imaging apparatus is managed by the support apparatus, the imaging apparatus need not manage the image.

(21) In accordance with still another aspect to solve the aforementioned problem, the present invention is the ultrasonic imaging apparatus as described regarding any one of (1)–(20), wherein the supporting means in the support apparatus comprises means for outputting an image captured by the imaging apparatus to an external device.

In the invention of this aspect, since external output of an image captured by the imaging apparatus is performed by the support apparatus, the imaging apparatus need not output the image to an external device.

(22) In accordance with still another aspect to solve the aforementioned problem, the present invention is the ultrasonic imaging apparatus as described regarding (21), wherein the means for outputting an image comprises means for insulating a primary and a secondary of an image output path.

In the invention of this aspect, since the primary and secondary of an image output path from the support apparatus are insulated, electric leakage across different systems can be prevented.

(23) In accordance with still another aspect to solve the aforementioned problem, the present invention is the ultrasonic imaging apparatus as described regarding any one of (1)–(22), wherein: the ultrasonic imaging means in the imaging apparatus comprises means for performing either or both of B-mode imaging or/and pulsed Doppler imaging; and the supporting means in the support apparatus comprises means for performing continuous wave Doppler imaging through the imaging apparatus.

In the invention of this aspect, since B-mode imaging and/or pulsed Doppler imaging are performed by the imaging apparatus and continuous wave Doppler imaging is performed by the support apparatus through the imaging apparatus, the imaging apparatus need not have most of the equipment for performing the continuous wave Doppler imaging.

(24) In accordance with still another aspect to solve the aforementioned problem, the present invention is the ultrasonic imaging apparatus as described regarding (23), wherein the means for performing continuous wave Doppler imaging comprises means for supplying a continuous wave transmit signal to the imaging apparatus.

In the invention of this aspect, since a continuous wave transmit signal for performing the continuous wave Doppler imaging is supplied by the support apparatus, the imaging apparatus need not have a continuous wave transmit signal generating section.

(25) In accordance with still another aspect to solve the aforementioned problem, the present invention is the ultrasonic imaging apparatus as described regarding (23) or (24), wherein the means for performing continuous wave Doppler imaging comprises means for gathering a continuous wave receive signal from the imaging apparatus.

In the invention of this aspect, since a continuous wave receive signal for performing the continuous wave Doppler imaging is gathered by the support apparatus, the imaging apparatus need not have a continuous wave receive signal processing section.

As described above in detail, the present invention can provide an ultrasonic imaging apparatus that responds to the requirement for both portability and versatility.

Further objects and advantages of the present invention will be apparent from the following description of the preferred embodiments of the invention as illustrated in the accompanying drawings.

DETAILED DESCRIPTION OF THE INVENTION

Figure 1:
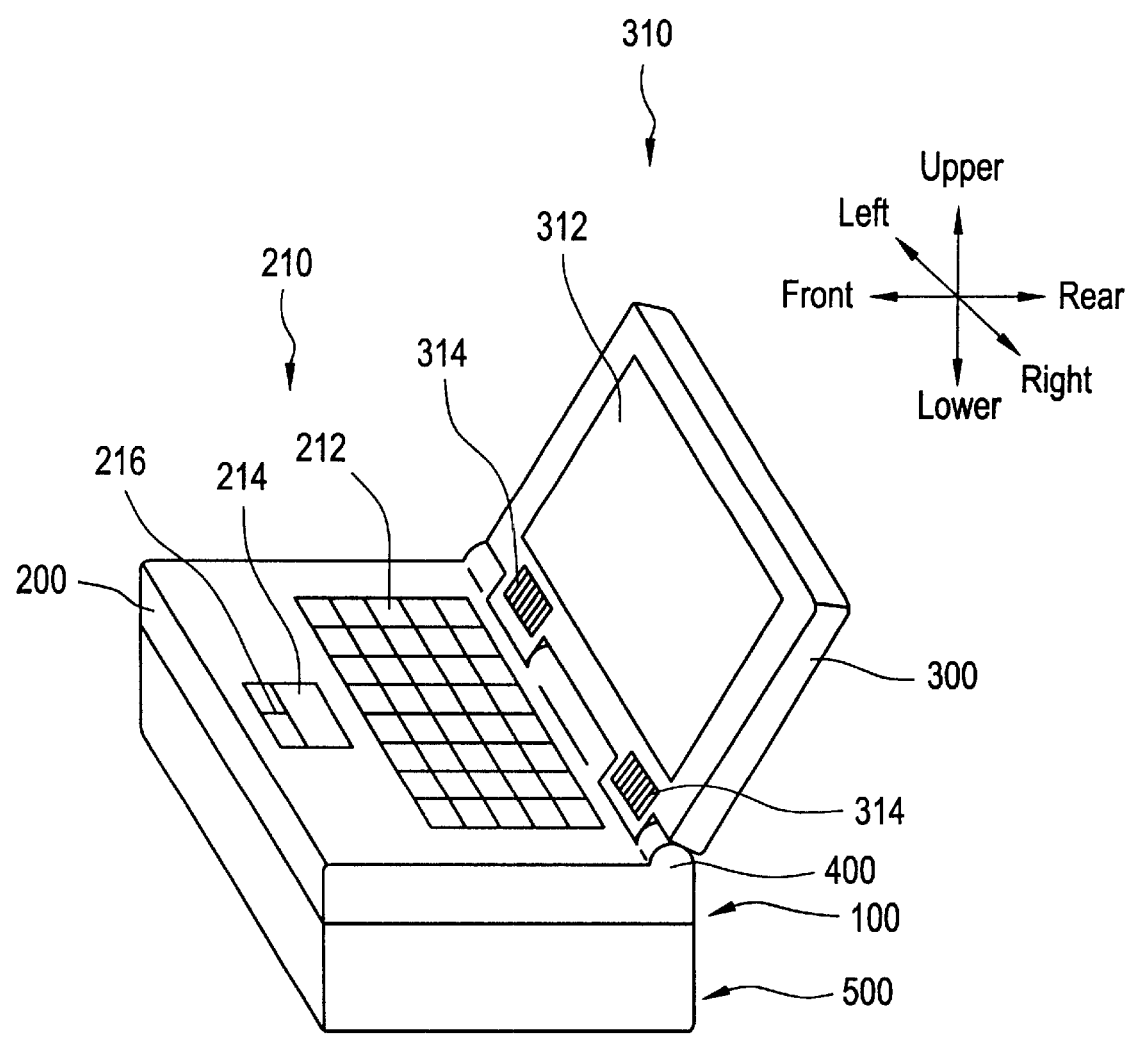
FIG. 1 is a schematic diagram illustrating the physical configuration of an apparatus in accordance with one embodiment of the present invention.

Several embodiments of the present invention will now be described in detail with reference to the accompanying drawings. It should be noted that the present invention is not limited to these embodiments. FIG. 1 schematically shows the physical configuration of a body of an ultrasonic imaging apparatus, which is an embodiment of the present invention. The configuration of the apparatus represents an embodiment of the apparatus in accordance with the present invention.

As shown in FIG. 1, the present apparatus is comprised of an imaging apparatus 100 and a support apparatus 500. The imaging apparatus 100 has basic ultrasonic imaging functions. The imaging apparatus 100 is an embodiment of the imaging apparatus in accordance with the present invention. The support apparatus 500 has functions for supporting the imaging apparatus 100 to extend the functions of the imaging apparatus 100. The support apparatus 500 is an embodiment of the support apparatus in accordance with the present invention.

With respect to the present apparatus, front and rear, right and left, and upper and lower directions are defined by arrows shown in FIG. 1. The imaging apparatus 100 is constructed by joining a generally box-shaped body 200 with a generally planar panel 300 via a hinge 400. The hinge 400 is provided between the upper portion of the rear end of the body 200 and the lower end portion of the panel 300.

The panel 300 can rotate relative to the body 200 around the hinge 400. The hinge 400 has a moderate frictional resistance to allow the panel 300 to be fixed at an arbitrary rotation angle.

Figure 2:
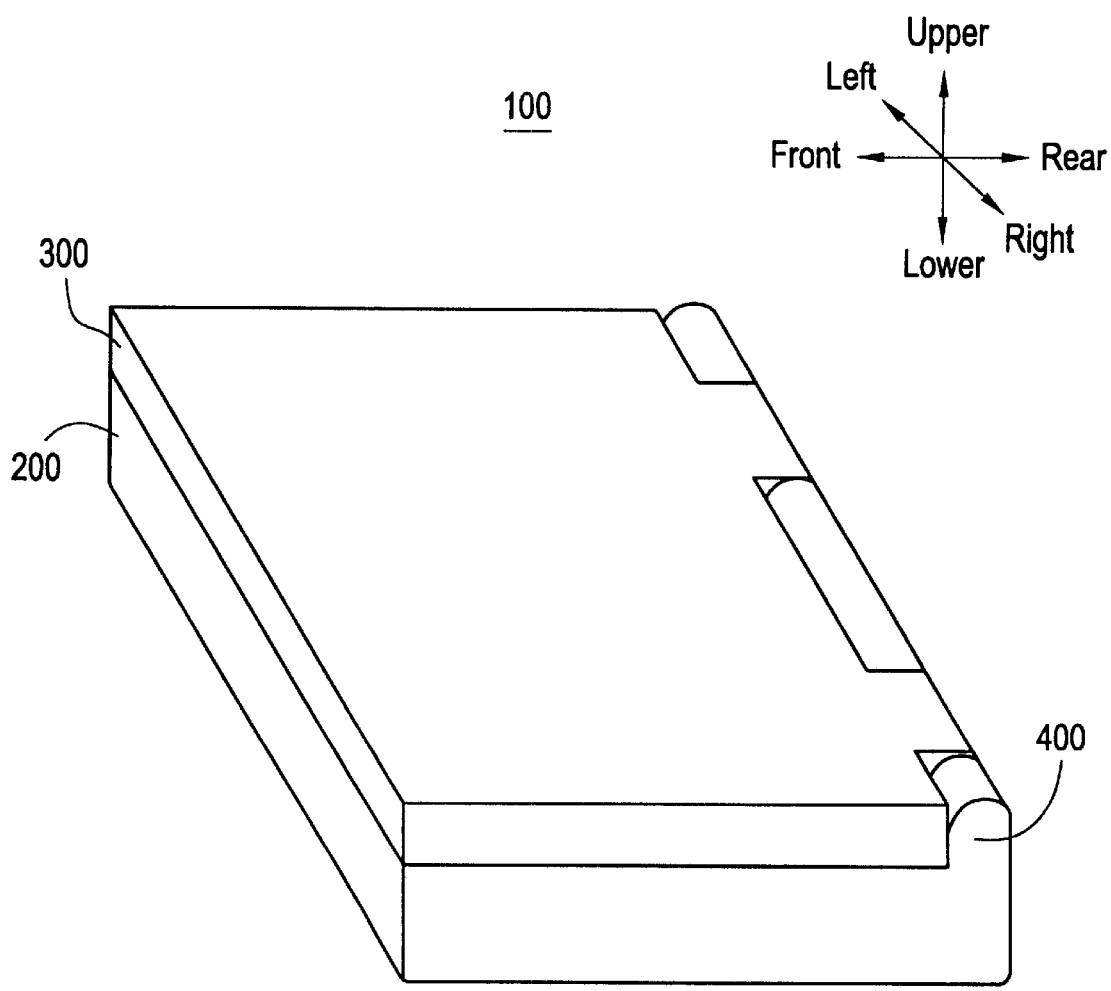
FIG. 2 is a schematic diagram illustrating part of the physical configuration of an apparatus in accordance with one embodiment of the present invention.

When the panel 300 is rotated counterclockwise to the maximum degree in the drawing, the panel 300 can be turned down on the upper surface of the body 200 as shown in FIG. 2. This condition will be sometimes referred to as the folded condition of the imaging apparatus 100 hereinbelow. Surfaces of the panel 300 and the body 200 that face each other in this condition constitute an embodiment of the pair of surfaces in accordance with the present invention.

The upper surface of the body 200 is configured as an operating section 210 of the present apparatus. The operating section 210 has a keyboard 212 and an input pad 214. The input pad 214 is provided with a pair of click buttons 216. The input pad 214 is used as a pointing device. The operating section 210 is an embodiment of the operating section in accordance with the present invention. A rear surface of the body 200, which is hidden in the drawing, is provided with a connector for connecting an ultrasonic probe.

A front surface of the panel 300 is configured as a display section 310. The display section 310 has an image display device and a pair of sound output devices 314. For the image display device 312, a flat panel display, such as, for example, an LCD (liquid crystal display), is employed. For the sound output devices 314, speakers, for example, are employed. The display section 310 is an embodiment of the display section in accordance with the present invention.

The support apparatus has a generally box-shaped outer shape. The upper surface of the support apparatus 500 has a shape adapted to the lower surface of the imaging apparatus 100. The imaging apparatus 100 is mounted over the support apparatus 500.

The imaging apparatus 100 is removable with respect to the support apparatus 500. Therefore, the imaging apparatus 100 can be removed from the support apparatus 500 and folded as shown in FIG. 2 for carrying.

The imaging apparatus 100 has a configuration such that it can perform basic ultrasonic imaging by itself. Thus, the ultrasonic imaging can be performed at a site to which the imaging apparatus 100 is carried. When the imaging apparatus 100 is used with the support apparatus 500 attached, precise imaging and so forth can be performed by employing the extended functions of the support apparatus 500. The support apparatus 500 is stationarily installed in a scan room or the like, and when precise imaging is to be performed, the imaging apparatus 100 is used with the support apparatus 500 attached in the scan room.

Figure 3:
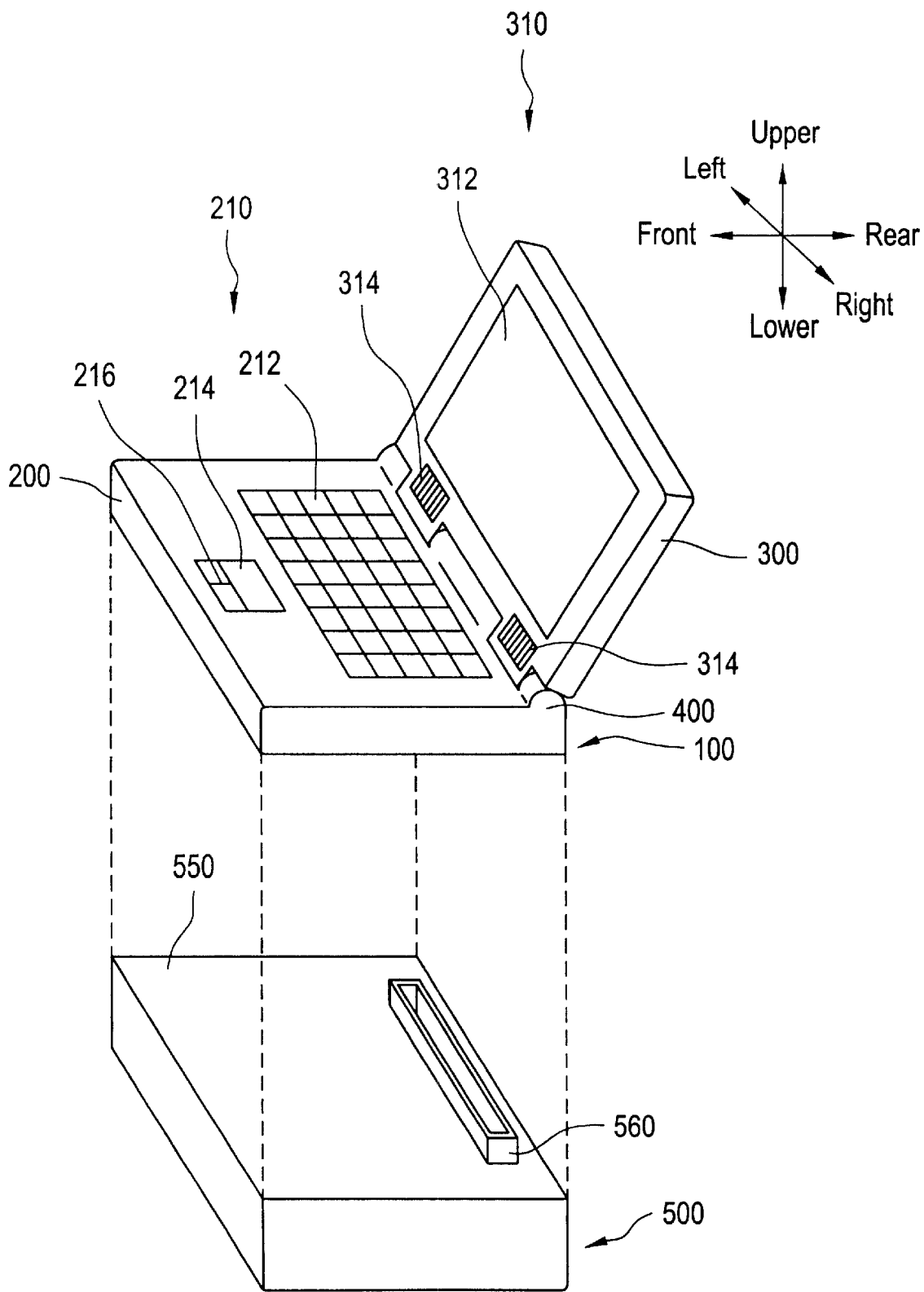
FIG. 3 is a schematic diagram illustrating the physical configuration of an apparatus in accordance with one embodiment of the present invention.

FIG. 3 shows the condition when the imaging apparatus 100 is removed from the support apparatus 500. As shown, the support apparatus 500 has a connector 560 on its upper surface, or a top portion 550. The connector 560 protrudes in the upper direction. The top portion 550 is an embodiment of the mounting portion in accordance with the present invention. The connector 560 is an embodiment of the connecting portion in accordance with the present invention. It is also an embodiment of the joining portion.

On the lower surface of the imaging apparatus 100 is provided a receptor 120 corresponding to the connector 560, which will be described later, and the connector 560 and the receptor 120 are electrically and mechanically joined when the imaging apparatus 100 is mounted over the support apparatus 500.

Figure 4:
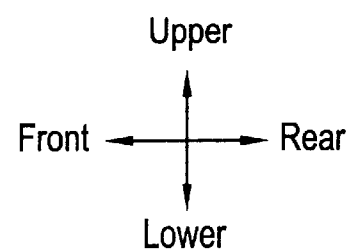
FIG. 4 is a schematic diagram illustrating the physical configuration of an apparatus in accordance with one embodiment of the present invention.
Figure 4:
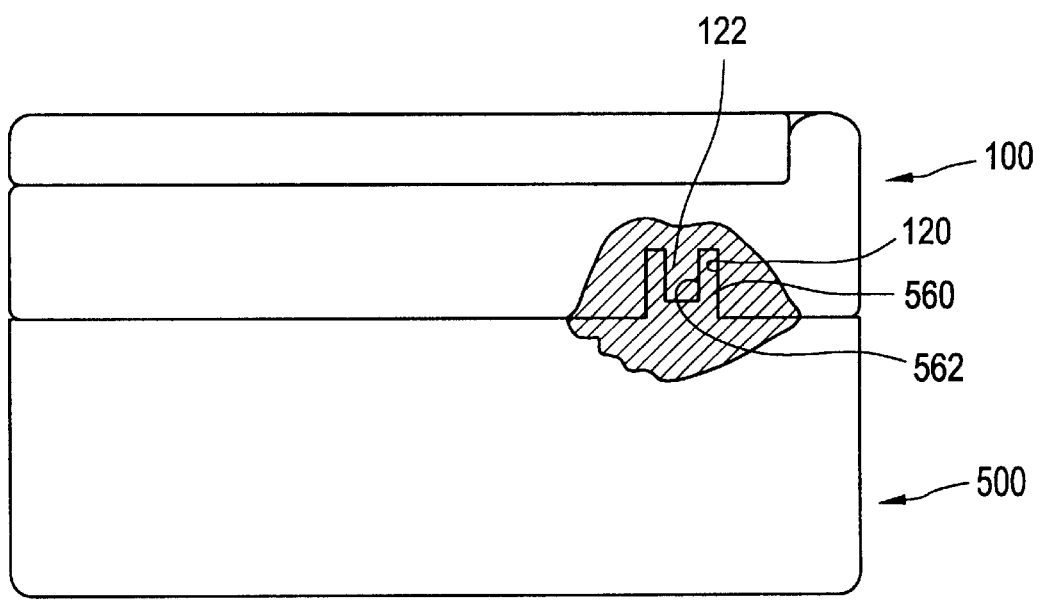

FIG. 4 schematically shows the joined condition of the connector 560 and the receptor 120. As shown, the receptor 120 is concave so as to receive the connector 560. The engagement between the receptor 120 and the connector 560 forms the mechanical joint of the imaging apparatus 100 and the support apparatus 500.

The connector 560 has a concave portion 562 extending inward from the tip to the base of the connector 560, and the receptor 120 has a protruding portion 122 protruding from the bottom to the entrance of the receptor 120. The protruding portion 122 can be fitted with the concave portion 562. The outer surface of the protruding portion 122 and the inner surface of the concave portion 562 are each provided with a plurality of electric contacts correspondingly, and contact between the corresponding electric contacts forms the electrical joint of the imaging apparatus 100 and the support apparatus 500.

Figure 5:
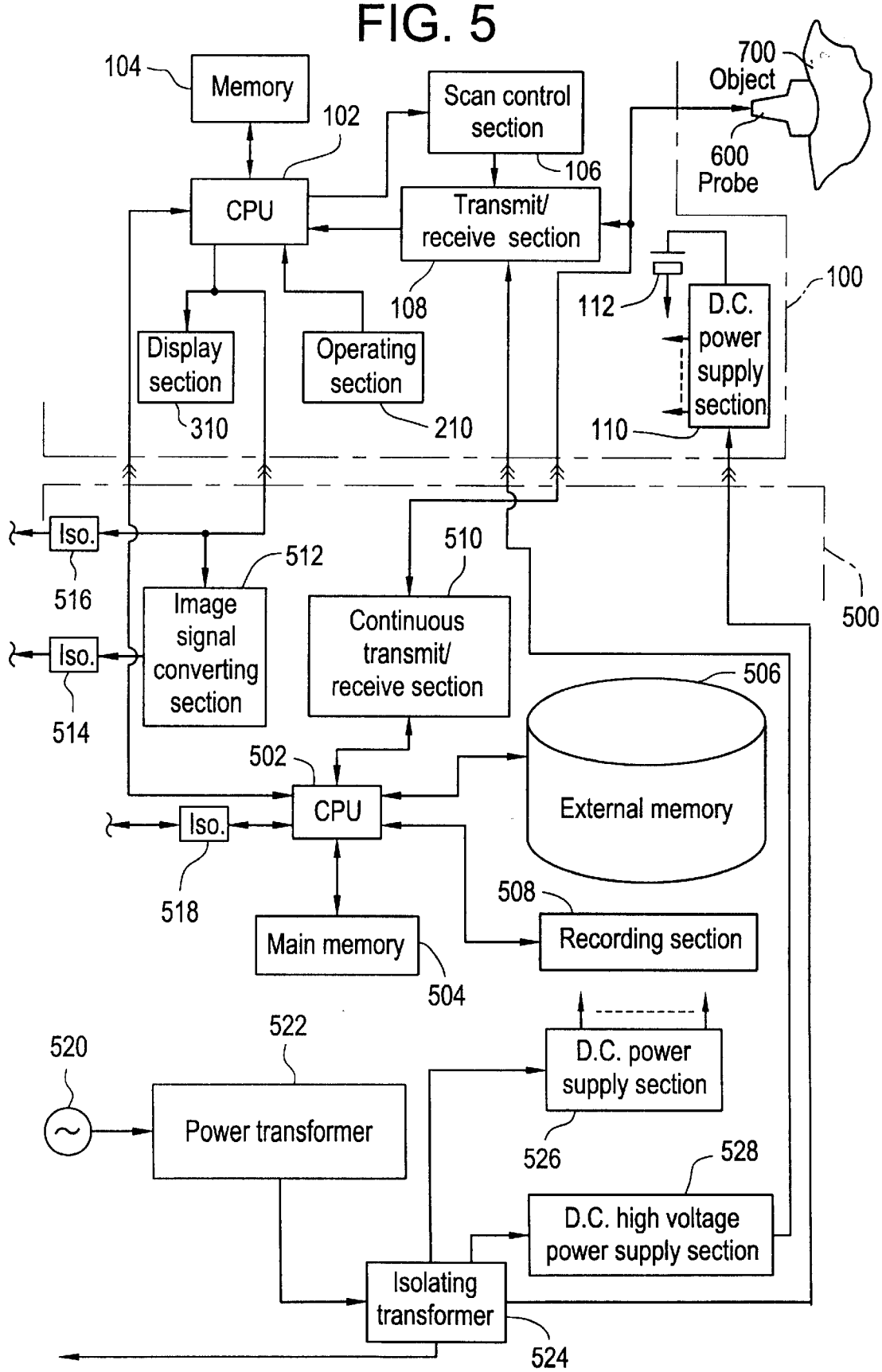
FIG. 5 is a block diagram illustrating the electrical configuration of an apparatus in accordance with one embodiment of the present invention.

FIG. 5 shows a block diagram of the electrical configuration of the present apparatus. As shown, the imaging apparatus 100 has a CPU (central processing unit) 102. The CPU 102 is connected with a memory 104. The memory 104 stores an OS (operating system), and a variety of application programs for ultrasonic imaging that operate under the OS. The CPU 102 is an embodiment of the CPU in accordance with the present invention.

For the OS, one that has a relatively simple configuration like those employed in, for example, a PDA (personal data assistant) is used. Therefore, the configuration of the CPU 102 may be simple and the capacity of the memory 104 may be small in proportion. The OS is an embodiment of the OS in accordance with the present invention.

The CPU is also connected with the operating section 210 and the display section 310. A user interactively operates the present apparatus via the operating section 210 and the display section 310.

The CPU 102 is also connected with a scan control section 106 and a transmitting/receiving section 108. The scan control section 106 is connected to the transmitting/receiving section 108. The transmitting/receiving section 108 is connected with an ultrasonic probe 600. The ultrasonic probe 600 is used by the user by abutting the probe 600 against an object to be imaged 700.

The transmitting/receiving section 108 scans the interior of the object 700 by a beam of pulsed ultrasound under control by the scan control section 106, and receives an echo of the ultrasound. The scan control section 106 performs scan control under control by the CPU 102. A B-mode imaging scan and a pulsed Doppler imaging scan are thus performed.

The echo receive signal from the transmitting/receiving section 108 is input to the CPU 102. The CPU 102 produces an image based on the input signal. Thus, a B-mode image and a pulsed Doppler image are produced.

The B-mode image and the pulsed Doppler image are displayed on the image display device 312 of the display section 310. The B-mode image represents a cross-sectional image of a tissue within the object 700. The pulsed Doppler image represents a flow velocity distribution etc. of blood flow within the object 700.

The imaging section 100 has a direct current power supply section 110. The direct current power supply section 110 supplies direct current power to the CPU 102, memory 104, scan control section 106, transmitting/receiving section 108, operating section 210 and display section 310. The direct current power supply section 110 is an embodiment of the direct current power supply in accordance with the present invention.

The direct current power supply section 110 is supplied with alternating current power from the support apparatus 500, and generates the direct current power based on the alternating current power. The direct current power supply section 110 incorporates therein a rechargeable battery 112, and also has a charging circuit for charging the rechargeable battery 112. The rechargeable battery 112 is an embodiment of the battery in accordance with the present invention.

When the imaging apparatus is removed from the support apparatus 500, the direct current power supply section 110 supplies the power from the rechargeable battery to the several sections. Thus, the imaging apparatus 100 can be used when it is removed from the support apparatus 500.

The support apparatus 500 has a CPU 502. The CPU 502 is an embodiment of the CPU in accordance with the present invention. The CPU 502 is connected with a main memory 504 and an external memory 506. For the main memory 504, a RAM (random access memory), for example, is employed. For the external memory 506, an HDD (hard disk drive) device, for example, is employed.

The external memory 506 stores an OS and a variety of application programs that operate under the OS. The OS is an embodiment of the OS in accordance with the present invention. The application programs are those for principally supporting the imaging apparatus 100 and extending its functions. The OS and application programs are loaded from the external memory 506 into the main memory 504 for execution.

Several kinds of data processed by the CPU 502 in the process of the execution of the application programs are stored in the external memory 506. The data include image data captured by the imaging apparatus 100.

For the OS, one with a full configuration, like those employed in, for example, a PC (personal computer) or EWS (engineering workstation), is used. Therefore, the configuration of the CPU 102 has high performance and the capacity of the main memory 504 and external memory 506 are large in proportion.

The CPU 502 is connected with the CPU 102. The connection between these CPU's is achieved by a data transfer line in compliance with, for example, the USB (universal serial bus) standard or IEEE 1394 standard. Thus, the CPU 502 and the CPU 102 can perform data communication with each other.

Instructions or the like input by the user from the operating section 210 for the CPU 502 are transmitted to the CPU 502 via the CPU 102. Thus, the CPU 502 can perform several kinds of support operations under the manipulation by the user, which operations will be described later. The portion consisting of the CPU 502 and CPU 102 connected with each other by the data transfer line is an embodiment of the means for performing data communication in accordance with the present invention.

The CPU 502 is connected with a continuous wave (CW) transmitting/receiving section 510. The continuous wave transmitting/receiving section 510 is connected with the ultrasonic probe 600 via the imaging apparatus 100. The continuous wave transmitting/receiving section 510 performs transmission of continuous wave ultrasound and reception of an echo of the ultrasound under control by the CPU 502.

It should be noted that the reception of the echo may be performed by the transmitting/receiving section 108 in the imaging apparatus 100. The continuous wave transmitting/receiving section 510 is an embodiment of the means for supplying a continuous wave transmit signal in accordance with the present invention. It is also an embodiment of the means for gathering a continuous wave receive signal.

The received continuous wave echo signal is input to the CPU 502. The CPU 502 determines a Doppler shift in the continuous wave echo receive signal, and performs frequency spectrum analysis on the Doppler shift. The obtained frequency spectrum is sent to the CPU 102 in the imaging apparatus 100 by data communication.

If the echo reception is performed by the transmitting/receiving section 108 in the imaging apparatus 100, the frequency spectrum analysis is performed by the CPU 102. The CPU 102 displays the frequency spectrum on the image display device 312 in the display section 310 as an image, and also outputs the Doppler sound from the sound output devices 314 as a sound.

Since the continuous wave transmitting/receiving section 510 has a relatively large amount of hardware, if the section 510 should be provided in the imaging apparatus 100, the imaging apparatus 100 would be scaled up and lose portability. Therefore, the continuous wave transmitting/receiving section 510 is provided in the support apparatus 500 that is not intended for carrying. Since diagnosis by the continuous wave Doppler is often performed when precise diagnosis is required, the continuous wave Doppler function may be omitted without substantial difficulty from the basic ultrasonic imaging functions that are performed at a site to which the imaging apparatus 100 is carried.

The image data captured by the imaging apparatus 100 is transferred to the CPU 502 in the support apparatus 500 by the CPU 102. The CPU 502 stores the image data in the external memory 506. Moreover, the frequency spectrum of the Doppler signal determined by the CPU 502 is also stored in the external memory 506. Thus, an imaging data file is formed in the external memory 506.

The CPU 502 is connected with a recording section 508. For the recording section 508, a recording device employing, for example, an MOD (magneto-optical disk) or DVD (digital versatile disk) as a recording medium is used. The CPU 502 records the imaging data file on the recording medium through the recording section 508 and saves the imaging data file. The recording section 508 is an embodiment of the means for recording an image in accordance with the present invention.

The imaging data file stored in the external memory 506 and the imaging data file recorded on the recording medium are managed by the CPU 502. The CPU 502 is an embodiment of the means for managing an image in accordance with the present invention. The imaging data file stored in the external memory 506 and the imaging data file recorded on the recording medium can be read out as required by the user, and displayed on the display section 310.

The support apparatus 500 has an image signal converting section 512. The image signal converting section 512 is for converting the format of an image signal input from the CPU 102 in the imaging apparatus 100.

The image signal input from the CPU 102, which complies with a standard suitable for the display section 310, such as VGA standard and SVGA standard, is converted into a television-type image signal compliant with, for example, NTSC (National Television System Committee) standard or PAL (phase alternation line) standard.

The converted signal is output to an external device by an isolator 514 with the input and output insulated. For the isolator 514, a photocoupler, for example, is employed. The VGA signal or the like before the conversion is output to the external device via an isolator 516. The isolators 514, 516 and 518 are embodiments of the means for insulating primary and secondary in accordance with the present invention.

The CPU 502 is capable of performing data communication with an external device through an isolator 518. For a data communication path to the external device, a USB or the like is employed, for example. The imaging data saved in the external memory 506 or the recording medium can thus be supplied to the external device. The CPU 102 is an embodiment of the means for performing data communication in accordance with the present invention. It is also an embodiment of the means for outputting an image to an external device.

The external devices include, for example, a network terminal, and the imaging data can be uploaded to a server and so forth in the network by the terminal. It will be easily recognized that several kinds of data and programs may moreover be downloaded from the server and so forth to the present apparatus.

By thus achieving insulation by the isolators 514, 516 and 518 for performing the external output of an image signal and the data communication, electric leakage etc. can be prevented from occurring between the present apparatus and the external device, thereby ensuring safety.

The support apparatus 500 has a power transformer 522 that is supplied with alternating current power from an alternating current power supply 520. The secondary of the power transformer 522 is connected with an isolating transformer 524. The isolating transformer 524 produces a plurality of alternating current power outputs that are individually insulated. By the isolating transformer 524, the plurality of outputs are insulated between the primary and the secondary, and insulated from one another, so that electric leakage is prevented from occurring among them. Safety is thus ensured.

The plurality of alternating current power outputs from the insulating transformer 524 are supplied to a direct current power supply section 526 and a direct current high voltage power supply section 528, and the direct current power supply section 110 in the imaging apparatus 100 and the external device.

The direct current power supply section 526 generates direct current power based on the supplied alternating current power. The generated direct current power is supplied to the CPU 502, main memory 504, external memory 506, recording section 508, continuous wave transmitting/receiving section 510 and image signal converting section 512.

The direct current high voltage power supply section 528 generates direct current high voltage power based on the supplied alternating current power. The generated direct current high voltage power is supplied to the transmitting/receiving section 108 in the imaging apparatus 100. The direct current high voltage power is used when a need to transmit high output ultrasonic pulses arises in performing, for example, precise imaging.

The portion consisting of the power transformer 522 and the isolating transformer 524 is an embodiment of the means for supplying power to the imaging apparatus in accordance with the present invention. It is also an embodiment of the means for supplying power to an external device. The direct current high voltage power supply section 528 is an embodiment of the means for supplying high voltage power to the imaging apparatus. The isolating transformer 524 is an embodiment of the means for insulating a primary and a secondary.

While the present invention is described with reference to preferred embodiments, various changes or substitutions may be made on these embodiments by those ordinarily skilled in the art pertinent to the present invention without departing from the scope of the present invention. Therefore, the scope of the present invention encompasses not only those embodiments described above but all the embodiments that fall within the scope of the appended claims.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic imaging apparatus comprising:

an imaging part including an ultrasonic imaging means and a pair of containers having a pair of surfaces foldable so that said pair of surfaces face each other in a folded state and are generally perpendicular to each other in a non-folded state, one of said pair of surfaces of a first of said pair of containers having a display screen and the other of said surfaces of a second of said pair of containers having a plurality of operating means thereon, wherein said first container having said one surface is shaped to be generally flat and of a thin first thickness and of a first rectangular dimension, and wherein said second container having said second surface is shaped to be generally flat and of a thin second thickness which is greater than said first thickness and of a rectangular shape of the same rectangular dimension as said first rectangular dimension; and a support part including a third container and support means for supporting extension of functions of said imaging part, said support part further comprising means for electrically connecting functions from said imaging part, and means for mechanically and movably connecting said support part to said imaging part, said third container being of said first rectangular dimension and of a thickness greater than said second thickness.

2. The apparatus of claim 1, wherein said imaging part and said support part each comprises:

an individual central processing unit;

means for supplying power; and means for performing communication therebeween.

3. The apparatus of claim 2, wherein said central processing unit of said imaging part is simpler than said central processing unit of said support part.

4. The apparatus of claim 2, wherein said means for performing communication comprises means for insulating a primary circuit and a secondary circuit of a data communication path.

5. The apparatus of claim 2, wherein said means for performing communication located in said support part comprises means for communicating with an external device.

6. The apparatus of claim 2, wherein said means for supplying power is either power of direct current, or in the alternative, power of alternating power, and is supplied to or from an external source, or in the alternative, from an internal soorce.

7. The apparatus of claim 6, wherein said means for supplying power comprises means for insulating primary and secondary circuits of a power supply path.

8. The apparatus of claim 2, wherein said power is of high voltage.

9. The apparatus of claim 2, wherein said support means comprises means for managing an image captured by said ultrasonic imaging means for said imaging part, means for recording said image, and means for outputting said image to an external device.

10. The apparatus of claim 9, wherein said means for outputting an image comprises means for insulating a primary circuit and a secondary circuit of an image output path.

11. The apparatus of claim 2, wherein said ultrasonic imaging means for said imaging part comprises means for performing either or both B-mode imaging and pulsed Doppler imaging, and wherein said support means comprises means for performing continuous Doppler imaging through said imaging part.

12. The apparatus of claim 11, wherein said means for performing continuous Doppler imaging comprises means for supplying a continuous transmit signal to said imaging part, and means for gathering a continuous receive signal from said imaging part.

\* \* \* \* \*